United States Patent
Reel et al.

[11] 4,329,283
[45] May 11, 1982

[54] HYDROXYPYRIDONE AZO DYESTUFFS

[75] Inventors: Henning Reel, Cologne; Klaus Leverenz, Leverkusen, both of Fed. Rep. of Germany

[73] Assignee: Bayer Aktiengesellschaft, Leverkusen, Fed. Rep. of Germany

[21] Appl. No.: 90,212

[22] Filed: Nov. 1, 1979

[30] Foreign Application Priority Data

Nov. 22, 1978 [DE] Fed. Rep. of Germany ....... 2850643

[51] Int. Cl.$^3$ ............................................. C09B 31/01
[52] U.S. Cl. .................................................. 260/156
[58] Field of Search ........................................ 260/156

[56] References Cited

U.S. PATENT DOCUMENTS

| | | | |
|---|---|---|---|
| 3,905,951 | 9/1975 | Berrie et al. | 260/156 |
| 3,952,122 | 4/1976 | de Kermadec et al. | 428/77 |
| 3,957,749 | 5/1976 | von Braohel et al. | 260/156 |
| 3,994,906 | 11/1976 | Hegar | 260/156 |
| 3,998,803 | 12/1976 | Burkhard et al. | 260/156 |

Primary Examiner—Winston A. Douglas
Assistant Examiner—Raymond Covington
Attorney, Agent, or Firm—Sprung, Horn, Kramer & Woods

[57] ABSTRACT

Disperse dyestuffs of the formula

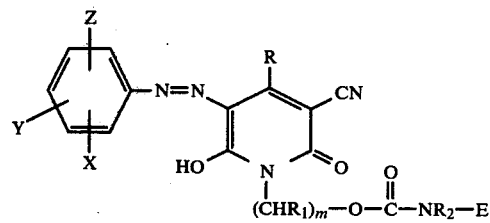

in which
R, $R_1$ and $R_2$ denotes alkyl,
E denotes A or B,
A denotes alkyl, alkenyl, cycloalkyl or aralkyl,
B denotes aryl,
m denotes the numbers 2–4,
Y and Z denotes R, Cl, Br or O—E and
X denotes R, Cl, Br, CHO, CO—E, COO—A, CONR—E, $SO_2$—E, $SO_2O$—B, $SO_2NR$—E, CN, $NO_2$, $CF_3$ or Y—$C_6H_4$—N=N—
with the proviso that Y and Z represent H, Cl, Br or O—E if X denotes 4-nitro, are especially suitable for the dyeing of polyester material since they give deep dyeings with high fastness to sublimation and interesting greenish-tinged yellow shade on that material.

4 Claims, No Drawings

HYDROXYPYRIDONE AZO DYESTUFFS

The invention relates to new azo disperse dyestuffs, processes for their preparation and their use for dyeing hydrophobic synthetic materials.

In one of their possible tautomeric forms, the dyestuffs, which are free from sulphonic acid groups and ammonium groups, have the formula (I)

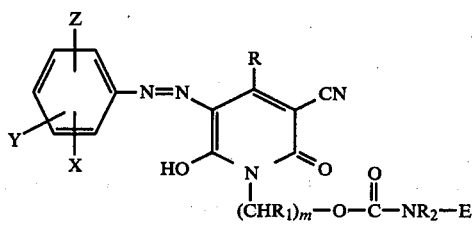

wherein $R$, $R_1$ and $R_2$ independently of one another denote hydrogen or $C_1$-$C_4$-alkyl, E denotes A or B, A denotes optionally substituted $C_1$-$C_8$-alkyl, $C_3$-$C_5$-alkenyl or cycloalkyl or carbocyclic aralkyl, B denotes optionally substituted aryl, m denotes the numbers 2-4, Y and Z independently of one another denote R, Cl, Br or O-E and X denotes R, Cl, Br, CHO, CO—E, COO—A, CONR—E, $SO_2$—E, $SO_2O$—B, $SO_2NR$—E, CN, $NO_2$, $CF_3$ or Y—$C_6H_4$—N≡N—, with the proviso that Y and Z represent H, Cl, Br or O—E if X denotes 4-nitro.

Suitable radicals R, $R_1$ and $R_2$ are, in addition to hydrogen, $CH_3$ and $C_2H_5$, linear or branched $C_3$- and $C_4$-alkyl radicals.

The straight-chain or branched alkyl radicals A have 1-8 C atoms and can, for example, be monosubstituted by CN, Cl, Br, $C_1$-$C_4$-alkoxy, phenoxy or R—($OC_2H_4$)$_r$- in which r denotes the numbers 2-4.

The preferred alkenyl radical A is the allyl radical.

Cyclohexyl or cyclopentyl radicals which are optionally substituted by methyl are suitable as cycloalkyl A.

Suitable aralkyl A is the benzyl, phenylethyl or phenylpropyl radical.

Suitable aryl B is phenyl, which can be substituted by $NO_2$ or monosubstituted to trisubstituted by $CH_3$, Cl, Br, $OCH_3$, $OC_2H_5$ or $CF_3$, or 1-naphthyl.

Preferred dyestuffs are those of the formula (II)

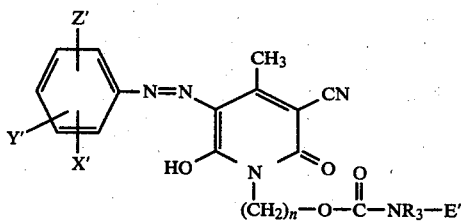

wherein n denotes the numbers 2 or 3, $R_3$ denotes hydrogen, $CH_3$ or $C_2H_5$, E' denotes A' or B', A' denotes $C_1$-$C_8$-alkyl which is optionally substituted by $C_1$-$C_4$-alkoxy, phenoxy, Cl or R—($OC_2H_4$)$_r$, B' denotes phenyl, tolyl, chlorophenyl or dichlorophenyl, Y' and Z' independently of one another denote hydrogen, $CH_3$, Cl, Br, $OCH_3$ or $OC_2H_5$, X' denotes Cl, Br, CN, $COCH_3$, $COC_6H_5$, COO—A', $CONR_3$—E', $SO_2CH_3$, $SO_2C_6H_5$, $SO_2O$—B', $SO_2NR_3$—E', phenylazo or $NO_2$ and R and r have the meaning indicated above, with the proviso that Y' and Z' denote Cl, Br, $OCH_3$ or $OC_2H_5$ if X' represents 4-nitro.

Particularly preferred dyestuffs are those of the formula (IIa)

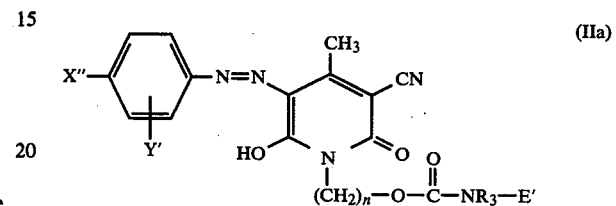

wherein

X" denotes Cl, $COCH_3$, $COC_6H_5$, COO—A', $CONR_3$—E', $SO_2CH_3$ $SO_2O$—B' or $SO_2NR_3$—E' and Y', E', n, $R_3$, A' and B' have the meaning indicated above.

Suitable $C_1$-$C_8$-alkyl radicals A' are, for example, $CH_3$, $C_2H_5$, n—$C_3H_7$, n—$C_4H_9$, n—$C_5H_{11}$, n—$C_6H_{13}$, n—$C_8H_{17}$, i—$C_3H_7$, i—$C_4H_9$, $CH_3CH(C_2H_5)C_4H_9$, i—$C_8H_{17}$, $CH_3OC_2H_4$—, $CH_3(OC_2H_4)_2$—, $C_2H_5OC_2H_4$—, $C_2H_5(OC_2H_4)_2$—, $C_2H_5(OC_2H_4)_3$—, $C_4H_9OC_2H_4$—, $C_6H_5OC_2H_4$—, Cl—($CH_2$)$_6$—, $CH_3OC_3H_6$—, $C_2H_5OC_3H_6$— or $C_6H_5OC_3H_7$—.

"Bulky" radicals, such as, for example, t-butyl, are preferably located in those positions where they do not effect any steric hindrance.

The new dyestuffs of the formula (I) are obtained by either diazotising an amine of the general formula (III)

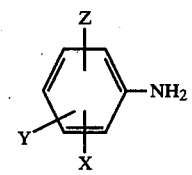

and coupling the diazo compound with a hydroxypyridone of the general formula (IV)

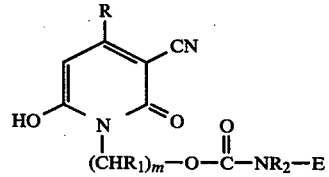

in which formulae

X, Y, Z, R, $R_1$, $R_2$, E and m have the meaning indicated above, or reacting an azo dyestuff of the general formula (V)

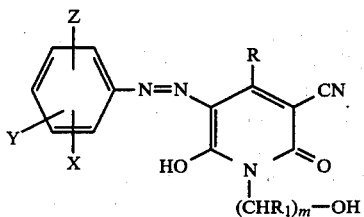

(V)

with an acylating agent of the general formula (VI) or (VII)

O=C=N—E (VI)

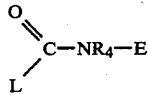

(VII)

in which

E has the meaning indicated above and
R₄ represents $C_1$-$C_4$-alkyl and
L represents halogen, preferably chlorine.

The reaction of the dyestuffs (V) with (VI) or (VII) is preferably carried out in organic solvents which are inert towards (VI)/(VII), such as, for example, acetone, methyl ethyl ketone, cyclohexanone, $CH_3CN$, toluene, chlorobenzene, dichlorobenzene or nitrobenzene, optionally with the addition of acid-binding agents, such as, for example, Na carbonate or Ca carbonate, MgO, trialkylamines or pyridine.

The coupling components of the general formula (IV) are known in some cases (compare DE-OS (German Published) No. 1,956,142=British Pat. No. 1,296,857, DE-OS (German Published) No. 1,901,711=U.S. Pat. No. 3,998,803, DE-OS (German Published) No. 1,932,806=U.S. Pat. No. 3,905,951, DE-OS (German Published) No. 2,157,229=British Pat. No. 1,360,749, DE-OS (German Published) No. 2,152,536=U.S. Pat. No. 3,952,122, DE-OS (German Published) No. 1,817,977=U.S. Pat. No. 3,957,749 and Japanese Published No. 51/37,919) or are obtained in a manner which is in itself known by either reacting the hydroxypyridones of the general formula (VIII)

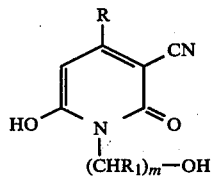

(VIII)

which are likewise known from the literature, with an acylating agent of the formula (VI) or (VII) or—preferably—reacting a cyanoacetic acid amide of the general formula (IX)

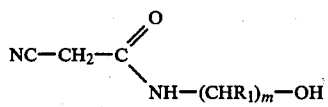

(IX)

with an acylating agent of the formula (VI) or (VII) to give the derivatives (X)

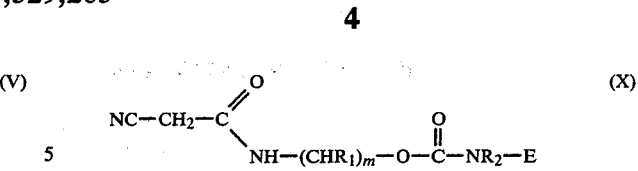

(X)

and then subjecting (X) to a condensation reaction with a β-ketocarboxylic acid ester of the general formula (XI)

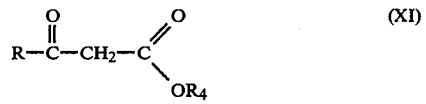

(XI)

in a manner which is in itself known, without the use of a solvent or in, for example, an alkanol, such as methanol, ethanol, isopropanol or n-butanol, and in the presence of a base, such as, for example, KOH, NaOH, triethylamine, 2-aminoethanol, pyridine, methylamine, 3-amino-1-propanol and the like, at elevated temperature, for example the reflux temperature, to give the hydroxypyridones (IV); in the formulae; R, $R_1$, $R_2$, $R_4$ and E have the meaning indicated above.

The alkali metal salts or amine salts of the coupling components which are thus obtained can be employed either direct or after neutralisation with acids, such as, for example, hydrochloric acid or acetic acid, for the coupling reaction.

Examples of amines of the formula (III) which can be used are: aniline, 2-, 3- and 4-amino-toluene, 2-, 4- and 5-amino-1,3-dimethyl-benzene, 4-amino-1,3,5-trimethyl-benzene, 4-amino-n-butyl-benzene, 3-amino-trifluoromethyl-benzene, 3- and 4-amino-1,2-dimethyl-benzene, 2,3- and 4-aminoanisole, 2,3- and 4-amino-n-butoxy-benzene, 2,3- and 4-aminophenetole, 4-amino-iso-octyl-oxy-benzene, 2-, 3- and 4-amino-diphenyl ether, 2-amino-1,4-dimethoxy-benzene, 2-amino-1,4-diethoxy-benzene, 2-amino-1,4-di-isopropoxybenzene, 2-, 3- and 4-chloroaniline, 2-, 3- and 4-bromoaniline, 2,3-, 2,4-, 2,5- and 3,4-dichloroaniline, 2,5-dibromoaniline, 2,4,5-, 2,4,6-, 3,4,5- and 3,4,6-trichloroaniline, 3-, 4-, 5- and 6-chloro-2-amino-toluene, 4-chloro-3-amino-toluene, 2-chloro-4-amino-toluene, 5-chloro-2-aminotrifluoromethyl-benzene, 4,5- and 4,6-dichloro-2-aminotoluene, 2,5- and 4,6-dichloro-3-amino-toluene, 2,5- and 3,5-dichloro-4-amino-toluene, 4,5,6-trichloro-2-amino-toluene, 4-chloro-2-amino-1,3-dimethyl-benzene, 2-, 3- and 4-amino-benzyl-methylsulphone, 4-aminophenyl-propyl-methylsulphone, 6-chloro-3-amino-anisole, 2-chloro-4-amino-anisole, 2-, 3- and 4-amino-benzonitrile, 1-amino-2-cyano-5-chlorobenzene, 2-chloro-4-amino-n-hexoxy-benzene, 3-chloro-4-amino-anisole, 2- and 4-nitroaniline, 5-nitro-4-amino-1,3-dimethyl-benzene, 6-nitro-3-amino-anisole, 3-nitro-4-aminoanisole, 3-nitro-4-amino-n-butoxy-benzene, 5-nitro-2-aminophenetole, 2-nitro-4-amino-phenetole, 3-nitro-4-amino-phenetole, 5-nitro-2-amino-1,4-dimethoxy-benzene, 5-nitro-2-amino-1,4-diethoxy-benzene, 2-chloro-4-nitroaniline, 2-bromo-4-nitroaniline, 4-chloro-2-nitroaniline, 4-bromo-2-nitroaniline, 2-, 3- and 4-amino-benzaldehyde, 2-, 3- and 4-amino-diphenyl ether, 2-amino-4-chloro- and 4,4'-dichlorodiphenyl ether, 2-, 3- and 4-amino-acetophenone, 4-amino-n-butyrophenone, 4-amino-n-caprophenone, 4-amino-α-ethyl-n-caprophenone, 2-, 3- and 4-amino-benzophenone, 2-, 3- and 4-amino-4'-methyl-, -4'-isopropyl-, 4'- n-butyl- and -4'-n-hexyl-benzophenone, 2-, 3- and 4-amino-2',4'-dimethylbenzophenone, 2-, 3- and 4-amino-4'-methoxy-benzophenone, 2-, 3- and 4-amino-4'-chloro-benzophenone, methyl and ethyl 2-, 3- and 4-amino-benzoate, n-butyl 2-, 3- and 4-aminobenzoate, n-decyl 2-, 3- and 4-amino-benzoate, iso-octyl 2-, 3- and 4-amino-benzoate, cyclohexyl 2-, 3- and 4-aminobenzoate, benzyl 2-, 3- and 4-amino-benzoate, β-methoxyethyl 2-, 3- and 4-amino-benzoate, β-ethoxy-ethyl 2-, 3- and 4-amino-benzoate, β-butoxy-ethyl 2-, 3- and 4-aminobenzoate, methyl-diglycol 2-, 3- and 4-amino-benzoate, ethyl-diglycol 2-, 3- and 4-amino-benzoate, methyl-triglycol 2-, 3- and 4-amino-benzoate, ethyl-triglycol 2-, 3- and 4-amino-benzoate, β-hydroxy-ethyl 2-, 3- and 4-amino-benzoate, β-hydroxy-propyl 2-, 3- and 4-amino-benzoate, γ-hydroxy-propyl 2-, 3- and 4-amino-benzoate, δ-hydroxybutyl 2-, 3- and 4-amino-benzoate, 2-, 3- and 4-aminobenzoic acid amide, 2-, 3- and 4-amino-benzoic acid monomethylamide, 2-, 3- and 4-amino-benzoic acid iso-octylamide, 2-, 3- and 4-amino-benzoic acid dimethylamide, 2-, 3- and 4-amino-benzoic acid ethylene imide, 2-, 3- and 4-aminobenzoic acid iso-propylamide, 2-, 3- and 4-amino-benzoic acid n-hexylamide, 2-, 3- and 4-amino-benzoic acid diethylamide, 2-, 3- and 4-amino-benzoic acid di-n-butylamide, phenyl 2-, 3- and 4-amino-phenyl-sulphonate, 4'-methylphenyl 2-, 3- and 4-amino-phenyl-sulphonate, 4'-n-butylphenyl 2-, 3- and 4-amino-phenyl-sulphonate, 4'-methoxyphenyl 2-, 3- and 4-amino-phenyl-sulphonate, 4'-chlorophenyl 2-, 3- and 4-amino-phenyl-sulphonate, 4'-methylphenyl 2-, 3- and 4-amino-benzene-sulphonate, 4'-n-butylphenyl 2-, 3- and 4-amino-benzene-sulphonate, 4'-methoxyphenyl 2-, 3- and 4-amino-benzene-sulphonate, 4-amino-phenylmethylsulphone, 4-amino-phenyl-n-butylsulphone, 4-aminophenyl-iso-octylsulphone, 4-amino-diphenylsulphone, 2-, 3- and 4-amino-benzene-sulphonic acid amide, 2-, 3- and 4-aminobenzene-sulphonic acid monomethylamide, 2-, 3- and 4-aminobenzene-sulphonic acid iso-octylamide, 2-, 3- and 4-amino-benzene-sulphonic acid dimethylamide, 2-, 3- and 4-aminobenzene-sulphonic acid ethylamide, 2-, 3- and 4-amino-benzene-sulphonic acid diethylamide, 2-, 3- and 4-amino-benzenesulphonic acid di-n-butylamide, 2-, 3- and 4-amino-benzenesulphonic acid morpholide, 2-, 3- and 4-amino-benzene-sulphonic acid cyclohexylamide, 2-, 3- and 4-amino-benzenesulphonic acid anilide, 2-, 3- and 4-amino-benzene-sulphonic acid N-methylanilide, 1-methyl-2-amino-benzene-4-sulphonic acid amide, 1-methyl-2-amino-benzene-4-sulphonic acid n-hexylamide, 1-methoxy-2-amino-benzene-4-sulphonic acid amide, 1-methoxy-2-amino-benzene-4-sulphonic acid dimethylamide, 1-methoxy-2-amino-benzene-4-sulphonic acid di-n-butylamide, 1-methoxy-2-amino-benzene-4-sulphonic acid N-methylanilide, 1-chloro-2-amino-benzene-4-sulphonic acid dimethylamide, 1-chloro-2-amino-benzene-5-sulphonic acid β-ethoxyethylamide, 1-chloro-3-amino-benzene-4-sulphonic acid amide, 1-chloro-4-amino-benzene-2-sulphonic acid dimethylamide, 4-amino-azobenzene, 2',3-dimethyl-4-amino-azobenzene, 2,3'-dimethyl-4-amino-azobenzene, 2,5-dimethyl-4-amino-azobenzene, 2-methyl-5-methoxy-4-amino-azobenzene and 2',3-dimethoxy-4-aminoazobenzene.

The dyestuffs according to the invention are suitable, especially in the finely dispersed form, for dyeing and printing structures made of synthetic materials, such as, for example, polyolefines, polyvinyl compounds, cellulose 2½-acetate, cellulose triacetate and especially polyester materials, for example polyethylene glycol terephthalate or analogous polymers. When applied by the conventional dyeing and printing processes, they give deep yellow dyeings and prints with very good fastness properties. For example, on the said types of fibre, the preferred dyestuffs of the present invention give dyeings which have an interesting greenish-tinged yellow shade and high fastness to sublimation.

In the examples which follow "parts" denote parts by weight.

EXAMPLE 1

N-(β-Hydroxyethyl)-3-cyano-4-methyl-6-hydroxy-pyrid-2-one 62.2 parts of ethanolamine are added dropwise at 10°–25° C. to 99 parts of methyl cyanoacetate. The mixture is stirred at room temperature for about a further 2 hours, 130 parts of ethyl acetoacetate are added, a further 62.2 parts of ethanolamine are then added dropwise in about 30 minutes, the mixture is heated at the boil (70°–75° C.) for 4–5 hours and the alcohols formed are then distilled off until a bottom temperature of at most 120° C. is reached. The dark brown, oily residue is diluted with water and the pH is adjusted to 7 with HCl.

According to the determination of the coupling value, this solution, which can be employed in this form for the synthesis of the dyestuff, contains 92–96% of theory of the desired product; only traces of impurities can be discerned by thin layer chromatography.

For isolation, only a small amount of water is added and the pH is adjusted to 2 with HCl; the bulk of the product then precipitates out and can be filtered off. Melting point 168°–170° C. (colourless needles after recrystallisation from water).

At lower pH values the hydrochloride is isolated: colourless needles on recrystallisation from water; sintering with a brown colouration above about 170° C., decomposition temperature 220° C.

The cyclisation can also be carried out in methanolic solution using KOH as an auxiliary base; in this case the K salt of the pyridone precipitates out.

EXAMPLE 2

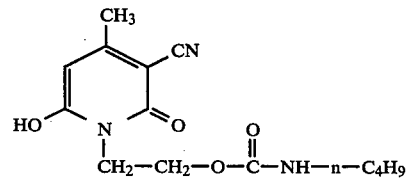

62.2 parts of ethanolamine are added dropwise at 10°–25° C. to 99 parts of methyl cyanoacetate. The mixture is stirred at room temperature for a further 1 hour and the methanol formed during the reaction is then distilled off under a water pump vacuum at a bottom temperature of at most 80° C., and 110 parts of n-butyl isocyanate are added rapidly dropwise at about 80° C.: initially there are two phases, which are converted to a homogeneous product by stirring for 2 hours at 105°–110° C.

At 80°–90° C., 130 parts of ethyl acetoacetate are then added rapidly and 62.2 parts of ethanolamine are added slowly.

The mixture is stirred for 5 hours at about 100° C. and is then discharged into about 1,000 parts of ice-water/300 parts of concentrated HCl: the product, which initially is oily, soon crystallises completely and is filtered off, washed with water and—if necessary—dried; according to thin layer chromatography it contains only traces of impurities.

Yield: about 220 parts (75% of theory)

Melting point 136° C. and after recrystallisation from H₂O 143° C.

EXAMPLE 3

15.1 parts of methyl p-aminobenzoate are dissolved in 60 parts of water and 30 parts of concentrated HCl and, after adding 100 parts of ice, diazotised at 0°-3° C. by the dropwise addition of one equivalent of 30% strength NaNO₂ solution. A little amidosulphonic acid is then added and if necessary the solution is clarified by the addition of 10 parts of kieselguhr.

19.4 parts of N-(β-hydroxyethyl)-3-cyano-4-methyl-6-hydroxypyrid-2-one are dissolved in about 200 parts of water with the addition of 40% NaOH, at pH 7-8. The mixture is cooled to 3°-8° C. by adding about 200 parts of ice and the above diazotisation mixture is allowed to run into this solution. During the addition, the pH value is kept at pH 5 by adding 40% strength NaOH dropwise at the same time, the mixture is then stirred for about a further 1 hour and, after filtering, washing the product with water and drying, about 34 parts (95% of theory) of the greenish-tinged yellow dyestuff are obtained.

This is boiled under reflux in about 300 parts of chlorobenzene with 10 parts of n-butyl isocyanate for 4-5 hours; according to thin layer chromatography the reaction has then ended. After cooling to room temperature, filtering, washing the product with methanol and drying, about 41 parts (90% total yield) of the dyestuff of the formula

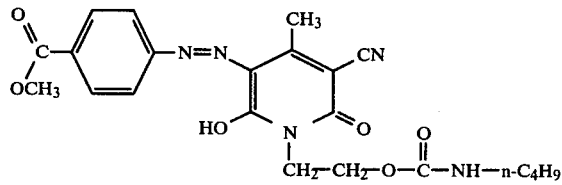

are obtained; this dyestuff dyes polyester fibres, for example, in a greenish-tinged yellow shade with outstanding fastness properties.

EXAMPLE 4

16.2 parts of 3,4-dichloroaniline are diazotised in aqueous/hydrochloric acid solution with NaNO₂ solution, by the procedure described in Example 3. The solution thus obtained is allowed to run into a suspension, which has been cooled to 3°-5° C., of 29.5 parts of the coupling component described in Example 2 in about 300 parts of water, the pH value being kept at pH 5 during the addition by adding 40% strength NaOH dropwise, and the mixture is then stirred for 3-4 hours. After filtering, washing the product with water and drying, about 44 parts (94% of theory) of the dyestuff of the formula

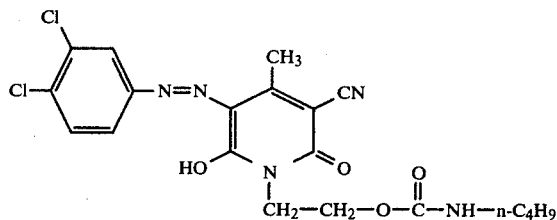

are obtained; this dyestuff dyes polyester materials, for example, in greenish-tinged yellow shades with outstanding fastness properties.

EXAMPLE 5

19.4 parts of dried N-(β-hydroxyethyl)-3-cyano-4-methyl-6-hydroxypyrid-2-one and 11 parts of n-butyl isocyanate in about 200 parts of diisopropyl ketone are heated at the boil for 5 hours. The solvent is then distilled off, the residue is taken up in about 300 parts of water, 200 parts of ice are added and a solution of diazotised o-nitroaniline, which has been prepared from 13.8 parts of o-nitroaniline by the procedure described in Example 3, is allowed to run in. During the addition, the pH is kept at 4.5-5.5 by adding 40% strength NaOH dropwise. After the coupling reaction has taken place, the reaction mixture is stirred for a further 4 hours and filtered, the material on the filter is washed with water and the dyestuff of the formula

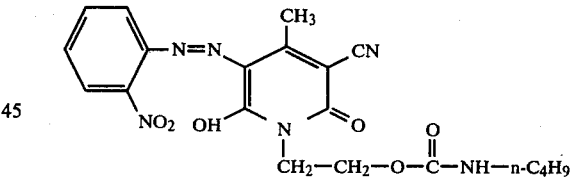

which is thus obtained is dried (about 40 g, 94% of theory). It dyes polyester materials, for example, in greenish-tinged yellow shades of outstanding fastness.

The dyestuffs listed in the tables which follow are prepared analogously to the above examples and serve to illustrate the present invention.

TABLE 1

| Example No. | X | E | m | Shade |
|---|---|---|---|---|
| 6 | 4-C₈H₁₇OOC— | CH₃ | 2 | greenish- |

TABLE 1-continued

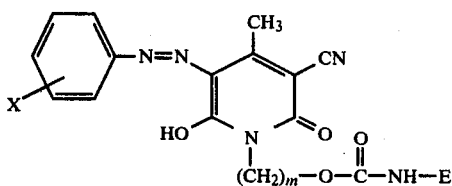

| Example No. | X | E | m | Shade |
|---|---|---|---|---|
| 7 | " | $C_2H_5$ | 3 | greenish-tinged yellow |
| 8 | " | $C_2H_5$ | 2 | greenish-tinged yellow |
| 9 | " | m-$CH_3$—$C_6H_4$ | 3 | greenish-tinged yellow |
| 10 | " | $C_4H_9$ | 2 | greenish-tinged yellow |
| 11 | " | $CH_2$—$C_6H_5$ | 2 | greenish-tinged yellow |
| 12 | " | $C_4H_9$ | 3 | greenish-tinged yellow |
| 13 | " | $CH_2$—$CH=CH_2$ | 2 | greenish-tinged yellow |
| 14 | " | $C_6H_5$ | 2 | greenish-tinged yellow |
| 15 | " | i-$C_4H_9$ | 2 | greenish-tinged yellow |
| 16 | " | $(CH_3)_2C_6H_5$ | 2 | greenish-tinged yellow |
| 17 | 4-$C_6H_{13}$OOC— | $CH_3$ | 2 | greenish-tinged yellow |
| 18 | " | $C_4H_9$ | 2 | greenish-tinged yellow |
| 19 | " | i-$C_4H_9$ | 2 | greenish-tinged yellow |
| 20 | " | $C_6H_5$ | 2 | greenish-tinged yellow |
| 21 | " | $C_4H_9$ | 3 | greenish-tinged yellow |
| 22 | 4-$C_4H_9$OOC— | $CH_3$ | 2 | greenish-tinged yellow |
| 23 | " | $C_4H_9$ | 2 | greenish-tinged yellow |
| 24 | " | $C_6H_5$ | 2 | greenish-tinged yellow |
| 25 | " | $C_2H_5$ | 3 | greenish-tinged yellow |
| 26 | 4-$C_3H_7$OOC— | $CH_3$ | 2 | greenish-tinged yellow |
| 27 | " | $C_4H_9$ | 2 | greenish-tinged yellow |
| 28 | " | o-$CH_3$—$C_6H_4$ | 2 | greenish-tinged yellow |
| 29 | " | $CH_3$ | 3 | greenish-tinged yellow |
| 30 | 4-$C_2H_5$OOC— | $C_4H_9$ | 2 | greenish-tinged yellow |
| 31 | " | $C_6H_{13}$ | 2 | greenish-tinged yellow |
| 32 | " | $C_6H_5$ | 2 | greenish-tinged yellow |
| 33 | 4-$CH_3$OOC | $CH_3$ | 2 | greenish-tinged yellow |
| 34 | " | i-$C_4H_9$ | 2 | greenish-tinged yellow |
| 35 | " | $C_6H_5$ | 2 | greenish-tinged yellow |
| 36 | 4-$CH_3OC_2H_4$OOC— | $CH_3$ | 2 | greenish-tinged yellow |
| 37 | " | $C_4H_9$ | 2 | greenish-tinged yellow |
| 38 | " | $C_6H_{13}$ | 2 | greenish-tinged yellow |
| 39 | " | $C_6H_5$ | 2 | greenish-tinged yellow |
| 40 | " | $C_4H_9$ | 3 | greenish-tinged yellow |
| 41 | 4-$CH_3(OC_2H_4)_2$OOC— | $C_4H_9$ | 2 | greenish- |

TABLE 1-continued

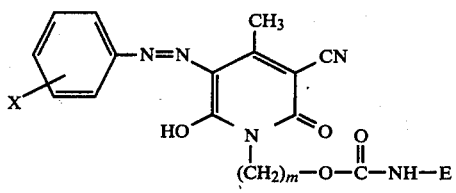

| Example No. | X | E | m | Shade |
|---|---|---|---|---|
| 42 | " | $C_3H_7$ | 2 | tinged yellow greenish-tinged yellow |
| 43 | " | $C_6H_5$ | 2 | greenish-tinged yellow |
| 44 | 2-$C_6H_{13}$OOC— | $C_4H_9$ | 2 | greenish-tinged yellow |
| 45 | 2-$C_2H_5$OOC— | $C_6H_5$ | 2 | greenish-tinged yellow |
| 46 | 2-$C_4H_9$OOC— | $CH_3$ | 3 | greenish-tinged yellow |
| 47 | 4-$CH_3$NHOC— | $CH_3$ | 2 | greenish-tinged yellow |
| 48 | " | $C_4H_9$ | 2 | greenish-tinged yellow |
| 49 | 4-$C_2H_5$NHOC— | $CH_3$ | 2 | greenish-tinged yellow |
| 50 | " | i-$C_4H_9$ | 2 | greenish-tinged yellow |
| 51 | " | $C_6H_5$ | 2 | greenish-tinged yellow |
| 52 | " | $CH_2$—$C_6H_5$ | 3 | greenish-tinged yellow |
| 53 | 4-$C_4H_9$NHOC— | $C_2H_5$ | 2 | greenish-tinged yellow |
| 54 | " | $C_4H_9$ | 2 | greenish-tinged yellow |
| 55 | " | p-$CH_3$—$C_6H_4$— | 2 | greenish-tinged yellow |
| 56 | 4-$C_6H_{13}$NHOC— | $CH_3$ | 2 | greenish-tinged yellow |
| 57 | " | $C_3H_7$ | 2 | greenish-tinged yellow |
| 58 | 4-$C_8H_{17}$NHOC— | $CH_3$ | 2 | greenish-tinged yellow |
| 59 | " | $C_2H_5$ | 2 | greenish-tinged yellow |
| 60 | " | $C_4H_9$ | 2 | greenish-tinged yellow |
| 61 | " | $C_4H_9$ | 3 | greenish-tinged yellow |
| 62 | " | $C_6H_5$ | 2 | greenish-tinged yellow |
| 63 | 4-$(C_2H_5)_2$NOC— | $C_4H_9$ | 2 | greenish-tinged yellow |
| 64 | " | $C_6H_5$ | 2 | greenish-tinged yellow |
| 65 | " | $CH_2$—$C_6H_5$ | 2 | greenish-tinged yellow |
| 66 | 4-$C_8H_{17}$NHO$_2$S— | $CH_3$ | 2 | greenish-tinged yellow |
| 67 | " | $C_4H_9$ | 2 | greenish-tinged yellow |
| 68 | " | $C_6H_5$ | 2 | greenish-tinged yellow |
| 69 | " | $C_2H_5$ | 3 | greenish-tinged yellow |
| 70 | " | m-$CH_3$—$C_6H_4$— | 2 | greenish-tinged yellow |
| 71 | 4-$C_6H_{13}$NH—$O_2$S— | i-$C_3H_7$ | 2 | greenish-tinged yellow |
| 72 | " | $C_4H_9$ | 2 | greenish-tinged yellow |
| 73 | " | m-$CH_3$—$C_6H_4$— | 2 | greenish-tinged yellow |
| 74 | 4-$C_4H_9$NH—$O_2$S— | $C_2H_5$ | 2 | greenish-tinged yellow |
| 75 | " | $CH_3$ | 2 | greenish-tinged yellow |
| 76 | 4-$C_2H_5$NH—$O_2$S— | $CH_3$ | 2 | greenish- |

TABLE 1-continued

[Structure: phenyl ring with X substituent, connected via N=N to a pyridine ring bearing CH₃, CN, HO, =O, and N-(CH₂)ₘ-O-C(=O)-NH-E groups]

| Example No. | X | E | m | Shade |
|---|---|---|---|---|
| 77 | " | C₄H₉ | 2 | greenish-tinged yellow |
| 78 | " | CH₂—C₆H₅ | 2 | greenish-tinged yellow |
| 79 | 4-(C₂H₅)₂N—O₂S— | CH₃ | 2 | greenish-tinged yellow |
| 80 | " | C₄H₉ | 2 | greenish-tinged yellow |
| 81 | " | C₆H₅ | 2 | greenish-tinged yellow |
| 82 | 4-CH₃O₂S— | C₄H₉ | 2 | greenish-tinged yellow |
| 83 | 4-C₆H₅O₂S— | CH₃ | 2 | greenish-tinged yellow |
| 84 | 4-C₆H₅O—O₂S— | CH₃ | 2 | greenish-tinged yellow |
| 85 | " | C₄H₉ | 2 | greenish-tinged yellow |
| 86 | " | C₆H₅ | 2 | greenish-tinged yellow |
| 87 | 4-C₆H₅NHO₂S— | CH₃ | 2 | greenish-tinged yellow |
| 88 | " | C₄H₉ | 3 | greenish-tinged yellow |
| 89 | 4-C₆H₅NHOC— | CH₃ | 2 | greenish-tinged yellow |
| 90 | " | C₆H₅ | 2 | greenish-tinged yellow |
| 91 | 4-CH₃CO— | CH₃ | 2 | greenish-tinged yellow |
| 92 | " | C₂H₅ | 2 | greenish-tinged yellow |
| 93 | " | C₄H₉ | 2 | greenish-tinged yellow |
| 94 | " | C₆H₅ | 2 | greenish-tinged yellow |
| 95 | 4-C₆H₅CO— | CH₃ | 2 | greenish-tinged yellow |
| 96 | " | i-C₃H₇ | 2 | greenish-tinged yellow |
| 97 | " | CH₃ | 3 | greenish-tinged yellow |
| 98 | 2-NO₂ | CH₃ | 2 | greenish-tinged yellow |
| 99 | " | i-C₃H₇ | 2 | greenish-tinged yellow |
| 100 | " | i-C₄H₉ | 2 | greenish-tinged yellow |
| 101 | " | C₄H₉ | 3 | greenish-tinged yellow |
| 102 | " | C₆H₁₃ | 2 | greenish-tinged yellow |
| 103 | " | C₆H₅ | 2 | greenish-tinged yellow |
| 104 | " | CH₂—C₆H₅ | 2 | greenish-tinged yellow |
| 105 | " | m-CH₃—C₆H₄ | 2 | greenish-tinged yellow |
| 106 | 4-NO₂ | CH₃ | 2 | yellow |
| 107 | " | C₄H₉ | 2 | yellow |
| 108 | " | C₆H₅ | 2 | yellow |
| 109 | 2-CN | C₄H₉ | 2 | greenish-tinged yellow |
| 110 | 4-CN | i-C₃H₇ | 2 | greenish-tinged yellow |
| 111 | 2-Cl | C₄H₉ | 2 | greenish-tinged yellow |
| 112 | " | C₆H₅ | 2 | greenish-tinged yellow |

TABLE 1-continued

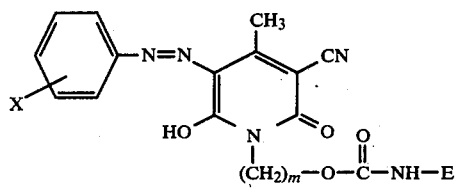

| Example No. | X | E | m | Shade |
|---|---|---|---|---|
| 113 | 3-Cl | $C_2H_5$ | 2 | greenish-tinged yellow |
| 114 | " | o-$CH_3$—$C_6H_4$ | 2 | greenish-tinged yellow |
| 115 | 4-Cl | $CH_3$ | 2 | greenish-tinged yellow |
| 116 | " | $CH_3$ | 3 | greenish-tinged yellow |
| 117 | " | $C_4H_9$ | 2 | greenish-tinged yellow |
| 118 | " | $C_6H_{13}$ | 2 | greenish-tinged yellow |
| 119 | " | $C_6H_5$ | 2 | greenish-tinged yellow |
| 120 | 2-Br | $C_2H_5$ | 3 | greenish-tinged yellow |
| 121 | " | $C_6H_5$ | 2 | greenish-tinged yellow |
| 122 | 2-$CF_3$ | $C_4H_9$ | 2 | greenish-tinged yellow |
| 123 | 4-$C_6H_5$—N=N— | $CH_3$ | 2 | golden yellow |
| 124 | " | $C_4H_9$ | 2 | golden yellow |

TABLE 2

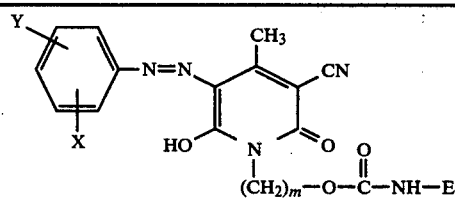

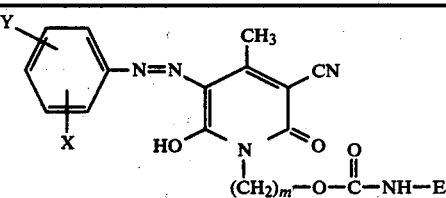

| Example No. | X | Y | E | m | Shade |
|---|---|---|---|---|---|
| 125 | 4-$NO_2$ | 2-$OCH_3$ | $CH_3$ | 2 | yellow |
| 126 | " | " | $C_4H_9$ | 2 | yellow |
| 127 | " | " | $C_6H_5$ | 3 | yellow |
| 128 | " | 2-$OC_2H_5$ | i-$C_4H_9$ | 2 | yellow |
| 129 | " | 2-$OC_6H_5$ | $CH_3$ | 2 | yellow |
| 130 | 2-Cl | 3-Cl | $C_4H_9$ | 2 | greenish-tinged yellow |
| 131 | " | " | $C_6H_5$ | 2 | greenish-tinged yellow |
| 132 | " | " | $CH_3$ | 2 | greenish-tinged yellow |
| 133 | " | 4-Cl | $CH_3$ | 2 | greenish-tinged yellow |
| 134 | " | " | $C_4H_9$ | 3 | greenish-tinged yellow |
| 135 | " | " | $C_6H_5$ | 2 | greenish-tinged yellow |
| 136 | " | 5-Cl | $CH_3$ | 2 | greenish-tinged yellow |
| 137 | " | " | $C_4H_9$ | 2 | greenish-tinged yellow |
| 138 | " | " | $C_6H_5$ | 2 | greenish-tinged yellow |
| 139 | " | " | $CH_2$—$C_6H_5$ | 3 | greenish-tinged yellow |
| 140 | " | " | i-$C_3H_7$ | 2 | greenish-tinged yellow |
| 141 | 2-Br | 5-Br | $CH_3$ | 2 | greenish-tinged yellow |
| 142 | " | " | $C_4H_9$ | 2 | greenish-tinged yellow |
| 143 | 2-Cl | 4-$CH_3$ | $C_4H_9$ | 2 | greenish-tinged yellow |
| 144 | " | 5-$CH_3$ | " | 2 | greenish-tinged yellow |
| 145 | " | 3-$CH_3$ | " | 2 | greenish-tinged yellow |
| 146 | 3-Cl | 4-Cl | $CH_3$ | 2 | greenish-tinged yellow |
| 147 | " | " | i-$C_3H_7$ | 2 | greenish-tinged yellow |
| 148 | " | " | $C_6H_{13}$ | 2 | greenish-tinged yellow |
| 149 | " | " | $C_6H_5$ | 3 | greenish-tinged yellow |
| 150 | 3-Cl | 5-Cl | $CH_3$ | 3 | greenish-tinged yellow |
| 151 | " | " | $C_4H_9$ | 2 | greenish-tinged yellow |
| 152 | " | " | $CH_2$—$C_6H_5$ | 2 | greenish-tinged yellow |
| 153 | " | " | $C_6H_5$ | 2 | greenish-tinged yellow |
| 154 | 2-Cl | 5-CN | $CH_3$ | 2 | greenish-tinged yellow |
| 155 | " | " | $C_4H_9$ | 2 | greenish-tinged yellow |
| 156 | 2-$NO_2$ | 4-$OCH_3$ | $CH_3$ | 2 | golden |

TABLE 2-continued

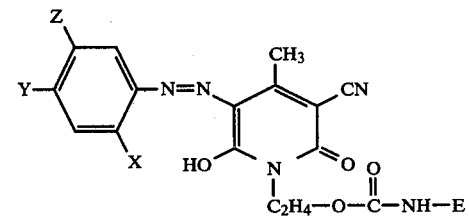

| Example No. | X | Y | E | m | Shade |
|---|---|---|---|---|---|
| 157 | " | " | C$_4$H$_9$ | 3 | golden yellow |
| 158 | " | 4-OC$_6$H$_5$ | C$_4$H$_9$ | 2 | golden yellow |
| 159 | 4-Cl | 2-NO$_2$ | CH$_3$ | 2 | golden yellow |
| 160 | " | " | C$_4$H$_9$ | 2 | golden yellow |
| 161 | " | " | C$_6$H$_5$ | 3 | golden yellow |
| 162 | 4-NO$_2$ | 2-Cl | C$_4$H$_9$ | 2 | golden yellow |
| 163 | " | " | C$_6$H$_5$ | 2 | golden yellow |
| 164 | 4-Cl | 3-CH$_3$ | CH$_3$ | 2 | greenish-tinged yellow |
| 165 | " | " | C$_4$H$_9$ | 2 | greenish-tinged yellow |
| 166 | " | " | C$_4$H$_9$ | 3 | greenish-tinged yellow |
| 167 | " | 2-CH$_3$ | C$_4$H$_9$ | 2 | greenish-tinged yellow |
| 168 | " | " | C$_6$H$_5$ | 2 | greenish-tinged yellow |
| 169 | 3-Cl | 4-CH$_3$ | CH$_3$ | 2 | greenish-tinged yellow |
| 170 | " | " | C$_4$H$_9$ | 2 | greenish-tinged yellow |

TABLE 3

| Example No. | X | Y | Z | E | m | Shade |
|---|---|---|---|---|---|---|
| 171 | 2-Cl | 4-Cl | 5-CH$_3$ | CH$_3$ | 2 | greenish-tinged yellow |
| 172 | " | " | " | C$_4$H$_9$ | 2 | greenish-tinged yellow |
| 173 | " | " | " | C$_6$H$_5$ | 2 | greenish-tinged yellow |
| 174 | " | " | " | i-C$_4$H$_9$ | 2 | greenish-tinged yellow |
| 175 | " | " | " | CH$_3$ | 3 | greenish-tinged yellow |
| 176 | 2-CH$_3$ | 4-NO$_2$ | 5-Cl | CH$_3$ | 2 | golden yellow |
| 177 | " | " | " | C$_4$H$_9$ | 2 | golden yellow |
| 178 | 2-Cl | 4-CH$_3$ | 5-CH$_3$ | CH$_3$ | 2 | greenish-tinged yellow |
| 179 | " | " | " | C$_2$H$_5$ | 2 | greenish-tinged yellow |
| 180 | " | " | " | C$_4$H$_9$ | 2 | greenish-tinged yellow |
| 181 | 4-Cl | 2-CH$_3$ | 5-CH$_3$ | C$_4$H$_9$ | 2 | greenish-tinged yellow |
| 182 | " | " | " | C$_6$H$_5$ | 3 | greenish-tinged yellow |
| 183 | 2-Cl | 4-Cl | 5-Cl | CH$_3$ | 3 | greenish-tinged yellow |
| 184 | " | " | " | C$_4$H$_9$ | 2 | yellow |
| 185 | " | " | " | C$_6$H$_5$ | 2 | yellow |

We claim:
1. An azo disperse dyestuff of the formula in which
E is C$_1$-C$_4$-alkyl,
X is H, Cl or NO$_2$,
Y is H, Cl, Cl$_1$-C$_4$-alkyl, OCH$_3$ or OC$_6$H$_5$, and
Z is H or Cl,
with the proviso that when X is H or Cl both Y and Z are Cl.

2. An azo dyestuff according to claim 1, in which X is H or Cl.

3. An azo dyestuff according to claim 1, in which X is H and E is n—C$_4$H$_9$.

4. An azo dyestuff according to claim 1, in which X is NO$_2$.

* * * * *